United States Patent
Shirai et al.

(10) Patent No.: US 9,194,041 B2
(45) Date of Patent: Nov. 24, 2015

(54) TRIS(DIALKYLAMIDE)ALUMINUM COMPOUND, AND METHOD FOR PRODUCING ALUMINUM-CONTAINING THIN FILM USING SAME

(71) Applicant: UBE INDUSTRIES, LTD., Ube-shi, Yamaguchi (JP)

(72) Inventors: Masashi Shirai, Ube (JP); Chihiro Hasegawa, Ube (JP); Hiroshi Nihei, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 14/355,893

(22) PCT Filed: Nov. 1, 2012

(86) PCT No.: PCT/JP2012/078399
§ 371 (c)(1),
(2) Date: May 2, 2014

(87) PCT Pub. No.: WO2013/065806
PCT Pub. Date: May 10, 2013

(65) Prior Publication Data
US 2014/0295084 A1   Oct. 2, 2014

(30) Foreign Application Priority Data

Nov. 2, 2011  (JP) ................... 2011-241025
Jan. 11, 2012  (JP) ................... 2012-003188
Jul. 5, 2012  (JP) ................... 2012-151757
Sep. 10, 2012  (JP) ................... 2012-198855

(51) Int. Cl.
*C07F 5/06*     (2006.01)
*C23C 16/20*    (2006.01)
(Continued)

(52) U.S. Cl.
CPC ............... *C23C 16/20* (2013.01); *C07F 5/069* (2013.02); *C23C 16/403* (2013.01); *C23C 16/4482* (2013.01)

(58) Field of Classification Search
None
See application file for complete search history.

(56) References Cited

U.S. PATENT DOCUMENTS

2002/0175393 A1  11/2002  Baum et al.
2004/0043632 A1   3/2004  Vaartstra
(Continued)

FOREIGN PATENT DOCUMENTS

JP   2004-529495   9/2004
JP   2005-537639  12/2005
(Continued)

OTHER PUBLICATIONS

Wade, C. R. et al, "Tris(dialkylamino)aluminums: Syntheses, characterization, volatility comparison and atomic layer deposition of alumina thin films", Materials Letters, 2007, vol. 61, No. 29, p. 5079-5082.
(Continued)

*Primary Examiner* — Joseph Miller, Jr.
(74) *Attorney, Agent, or Firm* — Nixon Peabody LLP; Jeffrey L. Costellia

(57) ABSTRACT

The present invention relates to a tris(dialkylamide)aluminum compound, and a method for producing an aluminum-containing thin film using the aluminum compound, the tris(dialkylamide)aluminum compound being represented by the formula (1):

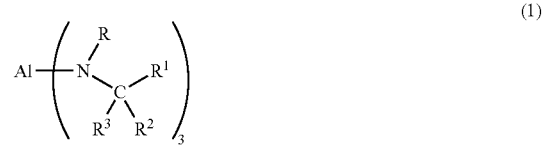

wherein
R represents a linear alkyl group having 1 to 6 carbon atoms; and
$R^1$, $R^2$ and $R^3$ may be the same as, or different from each other, and each independently represents hydrogen atom, or a linear or branched alkyl group having 1 to 6 carbon atoms, or $R^1$, $R^2$ and $R^3$ may be joined together to form a ring,
with the proviso that the compounds in which two or more of $R^1$, $R^2$ and $R^3$ are hydrogen atoms are excluded, and
three dialkylamide ligands may be the same as, or different from each other.

1 Claim, 1 Drawing Sheet

(51) Int. Cl.
*C23C 16/40* (2006.01)
*C23C 16/448* (2006.01)

(56) References Cited

U.S. PATENT DOCUMENTS

| | | |
|---|---|---|
| 2005/0003662 A1 | 1/2005 | Jursich et al. |
| 2008/0032062 A1 | 2/2008 | Meiere |
| 2008/0254216 A1 | 10/2008 | Kadota et al. |
| 2010/0099257 A1 | 4/2010 | Shin et al. |

FOREIGN PATENT DOCUMENTS

| | | |
|---|---|---|
| JP | 2006-526705 | 11/2006 |
| JP | 2007-138296 | 6/2007 |
| JP | 2009-542687 | 12/2009 |
| JP | 4716193 | 7/2011 |

OTHER PUBLICATIONS

International Preliminary Report on Patentability dated May 6, 2014 and Written Opinion dated Dec. 18, 2012 issued in International App. No. PCT/JP2012/078399.

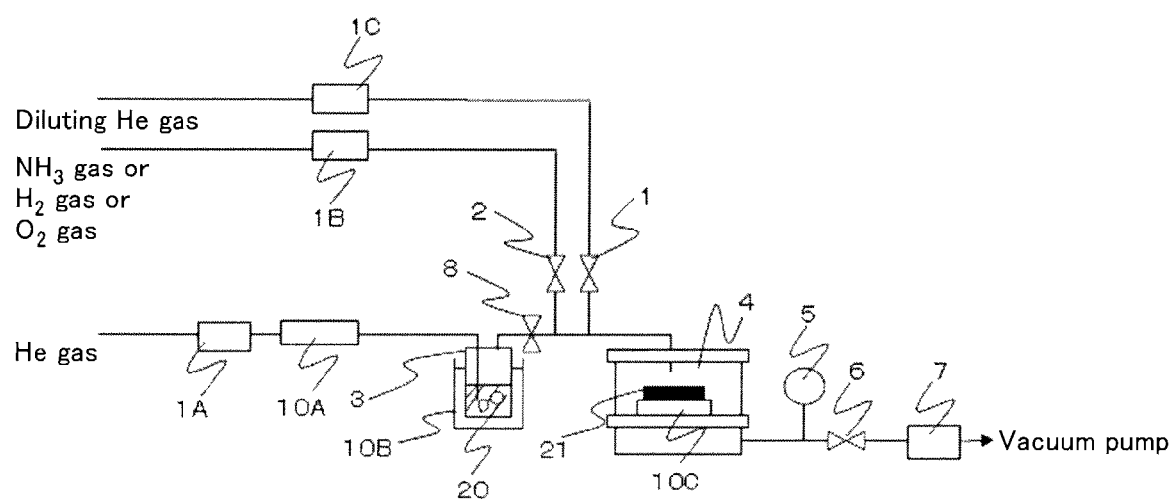

TRIS(DIALKYLAMIDE)ALUMINUM COMPOUND, AND METHOD FOR PRODUCING ALUMINUM-CONTAINING THIN FILM USING SAME

TECHNICAL FIELD

The present invention relates to a novel tris(dialkylamide) aluminum compound, and a method of producing an aluminum-containing thin film on an object by a chemical vapor deposition method (hereinafter, referred to as CVD method) using the aluminum compound.

BACKGROUND ART

Conventionally, various aluminum compounds such as alkyl aluminums, aluminum hydride, aluminum amide, aluminum alkoxide and aluminum diketonato, for example, have been studied as aluminum compounds to be used for the formation of aluminum-containing thin films (See, for example, Patent Literatures 1 to 3). Among them, trimethyl aluminum, aluminum hydride, and analogs thereof are mostly employed.

CITATION LIST

Patent Literature

Patent Literature 1: JP-A-2006-526705
Patent Literature 2: JP-B-4716193
Patent Literature 3: JP-A-2007-138296

SUMMARY OF INVENTION

Technical Problem

However, the conventional aluminum compounds do not necessarily have optimal properties such as vapor pressure, heat stability and reactivity for the formation of aluminum-containing thin film, and it may not be said that these compounds are adequate aluminum compounds for the formation of aluminum-containing thin film. In addition, trimethyl aluminum, which is most commonly employed, is pyrophoric, and therefore is very dangerous and difficult to handle. Accordingly, there is a need for aluminum compound having all properties such as vapor pressure, heat stability, reactivity and safety satisfying the requirements.

An object of the present invention is to solve the above-mentioned problems, and to provide an aluminum compound which is suitable for industrial use and from which an aluminum-containing thin film may be produced on an object by a simple method, and a method of producing an aluminum-containing thin film using the aluminum compound.

Solution to Problem

The present invention relates to the following items:

[1] A tris(dialkylamide)aluminum compound represented by the formula (1):

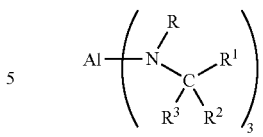

wherein
R represents a linear alkyl group having 1 to 6 carbon atoms; and
$R^1$, $R^2$ and $R^3$ may be the same as, or different from each other, and each independently represents hydrogen atom, or a linear or branched alkyl group having 1 to 6 carbon atoms, or $R^1$, $R^2$ and $R^3$ may be joined together to form a ring, with the proviso that the compounds in which two or more of $R^1$, $R^2$ and $R^3$ are hydrogen atoms are excluded, and
three dialkylamide ligands may be the same as, or different from each other.

[2] A method of producing a tris(dialkylamide)aluminum compound represented by the formula (1), comprising a step of:
reacting a trihalogeno aluminum represented by the formula (2):

$$AlX_3 \qquad (2)$$

wherein X represents a halogen atom,
with an alkali metal (dialkylamide) represented by the formula (3):

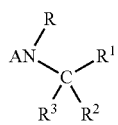

wherein A represents an alkali metal atom, and R, $R^1$, $R^2$ and $R^3$ are defined as above.

[3] A method of producing an aluminum-containing thin film by a chemical vapor deposition method (CVD method), wherein a tris(dialkylamide)aluminum compound represented by the formula (1) is used as an aluminum source.

Advantageous Effects of Invention

According to the present invention, there may be provided a novel tris(dialkylamide)aluminum compound, which is suitable for the formation of thin film by a CVD method, as well as a method of producing an aluminum-containing thin film using the aluminum compound.

BRIEF DESCRIPTION OF DRAWINGS

FIG. 1 is a diagram illustrating the construction of the vapor deposition apparatus, which was used in "Examples" for the formation of aluminum-containing thin film using the tris(dialkylamide)aluminum compound.

DESCRIPTION OF EMBODIMENTS

<Tris(dialkylamide)aluminum Compound of the Present Invention>

The tris(dialkylamide)aluminum compound of the present invention is represented by the formula (1).

In the formula (1), R represents a linear alkyl group having 1 to 6 carbon atoms such as methyl, ethyl, n-propyl, n-butyl, n-pentyl and n-hexyl. R may be preferably a linear alkyl group having 1 to 4 carbon atoms, more preferably a linear alkyl group having 1 to 2 carbon atoms (methyl, ethyl).

$R^1$, $R^2$ and $R^3$ may be the same as, or different from each other, and each independently represents hydrogen atom, or a linear or branched alkyl group having 1 to 6 carbon atoms such as methyl, ethyl, n-propyl, isopropyl, t-butyl, t-pentyl, neopentyl and hexyl. $R^1$, $R^2$ and $R^3$ may be joined together to form a ring, and the ring formed may be preferably cyclopropyl, cyclopentyl or cyclohexyl, particularly preferably cyclopropyl or cyclopentyl. However, the cases where two or more of $R^1$, $R^2$ and $R^3$ are hydrogen atoms are excluded. $R^1$, $R^2$ and $R^3$ may be preferably hydrogen atom, or a linear or branched alkyl group having 1 to 6 carbon atoms, more preferably hydrogen atom, or a linear or branched alkyl group having 1 to 3 carbon atoms, more preferably hydrogen atom, or an alkyl group having 1 to 2 carbon atoms (methyl, ethyl), particularly preferably hydrogen atom, or methyl. However, at least two of $R^1$, $R^2$ and $R^3$ are alkyl groups.

Part of, or all of three dialkylamide ligands:

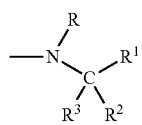

may be different from each other.

In one preferred embodiment of the present invention, R is a linear alkyl group having 1 to 4 carbon atoms, more preferably a linear alkyl group having 1 to 2 carbon atoms, and $R^1$, $R^2$ and $R^3$ are hydrogen atom, or a linear or branched alkyl group having 1 to 3 carbon atoms, more preferably hydrogen atom, or an alkyl group having 1 to 2 carbon atoms, particularly preferably hydrogen atom, or methyl. (However, the cases where two or more of $R^1$, $R^2$ and $R^3$ are hydrogen atoms are excluded.)

Examples of the aluminum compound of the present invention include the compounds represented by the following formulas (6) to (37).

(6)
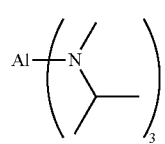

(7)
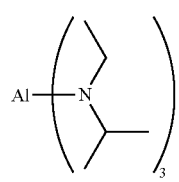

(8)
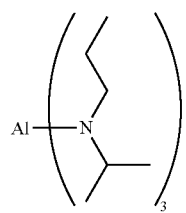

(9)
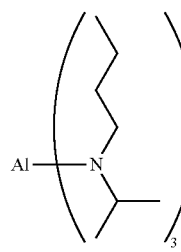

(10)
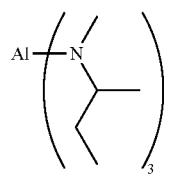

(11)
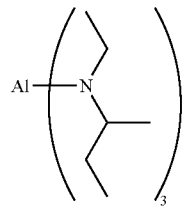

(12)
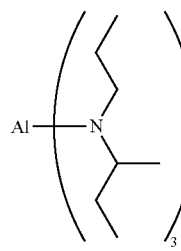

(13)
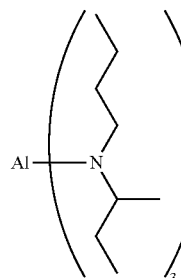

(14)
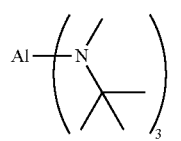

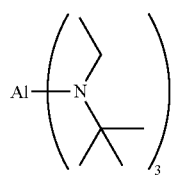 (15)
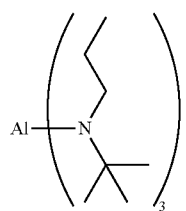 (16)
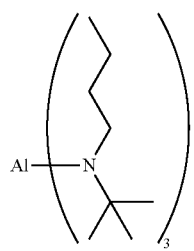 (17)
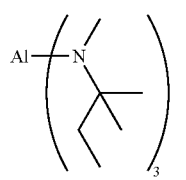 (18)
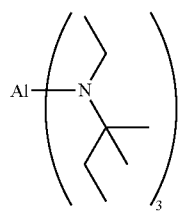 (19)
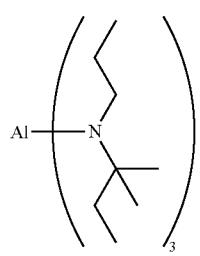 (20)
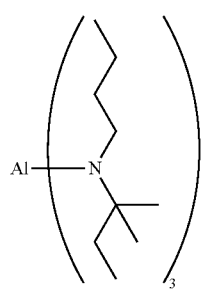 (21)
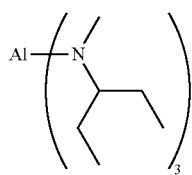 (22)
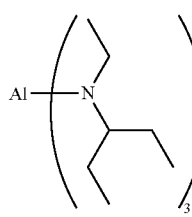 (23)
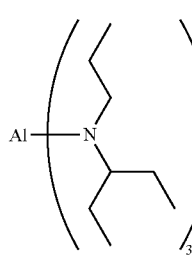 (24)
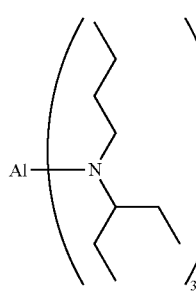 (25)
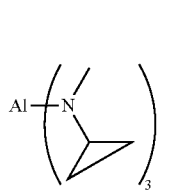 (26)
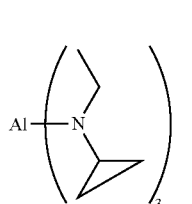 (27)
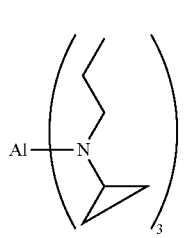 (28)

(29) 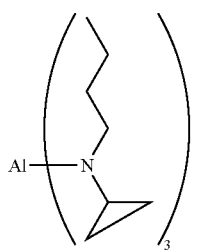

(30) 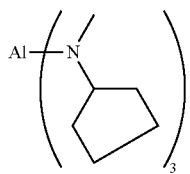

(31) 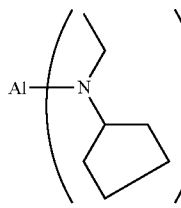

(32) 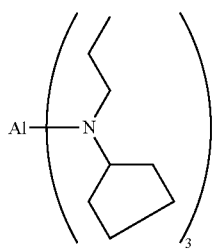

(33) 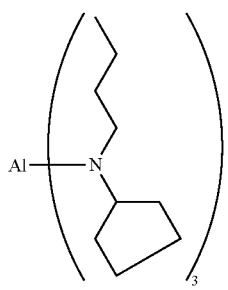

(34) 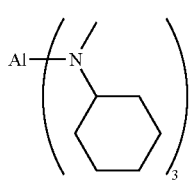

(35) 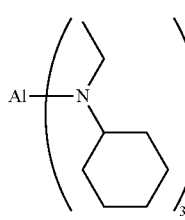

(36) 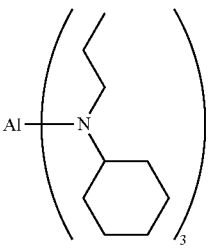

(37) 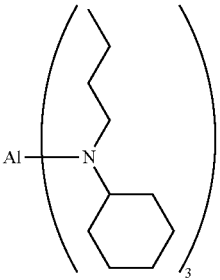

<Method of Producing Tris(Dialkylamide)Aluminum Compound of the Present Invention>

The tris(dialkylamide)aluminum compound of the present invention may be synthesized by either of the methods (hereinafter, sometimes referred to as "reaction(s) of the present invention") as shown in the following scheme (A) or (B).

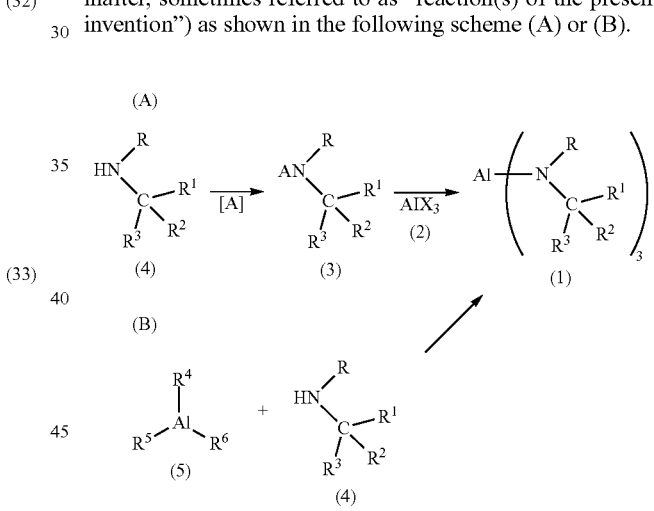

wherein

R, $R^1$, $R^2$ and $R^3$ are defined as above;

X represents a halogen atom;

A represents an alkali metal atom; and $R^4$, $R^5$ and $R^6$ may be the same as, or different from each other, and each independently represents hydrogen atom, or a linear or branched alkyl group having 1 to 10 carbon atoms; and

[A] represents an alkali metal, or an alkali metal compound.

<Method (A)>

The method (A) of the present invention is a method in which alkali metal (dialkylamide) (hereinafter, sometimes referred to as "dialkylamide compound") is synthesized from dialkylamine and alkali metal, or alternatively, alkali metal compound, and then the tris(dialkylamide)aluminum compound of the present invention is synthesized by reacting the alkali metal (dialkylamide) with trihalogeno aluminum.

The dialkylamine to be used in the reaction (A) of the present invention is represented by the formula (4). In the formula (4), R, $R^1$, $R^2$ and $R^3$ correspond to R, $R^1$, $R^2$ and $R^3$ in the formula (1), respectively, and are defined as above.

Preferable examples of the dialkylamine to be used in the reaction (A) of the present invention include methyl isopropyl amine, ethyl isopropyl amine, n-propyl isopropyl amine, n-butyl isopropyl amine, methyl-t-butyl amine, ethyl-t-butyl amine, n-propyl-t-butyl amine, n-butyl-t-butyl amine, methyl-s-butyl amine, ethyl-s-butyl amine, n-propyl-s-butyl amine, n-butyl-s-butyl amine, methyl-t-amyl amine, ethyl-t-amyl amine, n-propyl-t-amyl amine and n-butyl-t-amyl amine. Among them, methyl isopropyl amine, ethyl isopropyl amine, n-propyl isopropyl amine, methyl-t-butyl amine, ethyl-t-butyl amine, n-propyl-t-butyl amine, methyl-s-butyl amine, ethyl-s-butyl amine or n-propyl-s-butyl amine may be more preferably used.

The alkali metal (dialkylamide) to be synthesized in the reaction (A) of the present invention is represented by the formula (3). In the formula (3), A represents an alkali metal atom such as lithium atom and sodium atom.

Examples of the alkali metal or alkali metal compound to be used in the reaction (A) of the present invention include methyl lithium, ethyl lithium, n-butyl lithium, s-butyl lithium, t-butyl lithium, metal sodium and sodium hydride. Among them, n-butyl lithium may be preferably used.

In addition, alkaline earth metal such as magnesium, or alkaline earth metal compound such as diethyl magnesium, ethyl butyl magnesium and dibutyl magnesium may be used instead of the alkali metal or alkali metal compound.

The amount of the alkali metal or alkali metal compound to be used may be preferably from 0.4 mole to 1.4 mole, more preferably from 0.6 mole to 1.2 mole, per mole of the dialkylamine.

In the reaction (A) of the present invention, the dialkylamide compound represented by the formula (3) is synthesized from dialkylamine and alkali metal, or alternatively, alkali metal compound, and then the tris(dialkylamide)aluminum compound of the present invention is synthesized by reacting the synthesized dialkylamide compound with trihalogeno aluminum.

In addition, the dialkylamide compound (alkaline earth metal to which two dialkylamides are bound) may be synthesized and reacted using alkaline earth metal such as magnesium, or alkaline earth metal compound, instead of the alkali metal or alkali metal compound.

The trihalogeno aluminum to be used in the reaction (A) of the present invention is represented by the formula (2). In the formula (2), X represents a halogen atom such as fluorine atom, chlorine atom, bromine atom and iodine atom, preferably chlorine atom. In other words, the trihalogeno aluminum to be used may be preferably aluminum chloride.

The amount of the trihalogeno aluminum to be used may be preferably from 0.1 mole to 0.6 mole, more preferably from 0.1 mole to 0.4 mole, per mole of the dialkylamide compound.

The reaction (A) of the present invention may be preferably conducted in an organic solvent. The organic solvent to be used is not limited as long as it does not inhibit the reaction. Examples thereof include ethers such as diethyl ether, tetrahydrofuran, dimethoxyethane, dioxane, cyclopentyl methyl ether, t-butyl methyl ether and 4-methyl tetrahydropyran; aliphatic hydrocarbons such as hexane, heptane, cyclohexane, methylcyclohexane and ethylcyclohexane; and aromatic hydrocarbons such as toluene and xylene. An ether, an aliphatic hydrocarbon, or a mixture of an ether and an aliphatic hydrocarbon may be suitably used. These organic solvents may be used alone or in combination of two or more types thereof.

The amount of the organic solvent to be used may be preferably from 1 g to 100 g, more preferably from 5 g to 50 g, per gram (g) of the trihalogeno aluminum.

The reaction (A) of the present invention may be conducted, for example, by a method in which dialkylamine and alkali metal, or alternatively, alkali metal compound, and an organic solvent are mixed, and the resultant mixture is reacted while stirring to produce dialkylamide compound, and then trihalogeno aluminum is added to the mixture, and the resultant mixture is further reacted while stirring. The reaction temperature may be preferably from −100° C. to 100° C., more preferably from −80° C. to 40° C. There are no particular restrictions to the reaction pressure. The dialkylamide compound may be isolated from the reaction solution prior to the reaction with trihalogeno aluminum, or alternatively, the reaction solution may be used without isolating the dialkylamide compound as described above, and the reaction solution may be used without any treatment, or after exchange, removal and/or addition of organic solvent, as appropriate.

<Method (B)>

The method (B) is a method in which the tris(dialkylamide) aluminum compound is synthesized by reacting dialkylamine with aluminum hydride compound, or alternatively, alkyl aluminum compound.

The aluminum hydride compound or the alkyl aluminum compound to be used in the reaction (B) of the present invention is represented by the formula (5). In the formula (5), $R^4$, $R^5$ and $R^6$ each independently represents hydrogen atom, or a linear or branched alkyl group having 1 to 10 carbon atoms such as methyl, ethyl, n-propyl, isopropyl, n-butyl, isobutyl, t-butyl, n-pentyl, t-pentyl, neopentyl and n-decyl. $R^4$, $R^5$ and $R^6$ may be the same as, or different from each other.

The aluminum hydride compound or the alkyl aluminum compound to be used in the reaction (B) of the present invention may be a commercially available product, and may be prepared from a metallic aluminum by a known method. In the reaction (B) of the present invention, aluminum hydride, lithium aluminum hydride, sodium aluminum hydride, trimethyl aluminum, triethyl aluminum, or the like may be preferably used.

The dialkylamine to be used in the reaction (B) of the present invention is represented by the formula (4). In the formula (4), R, $R^1$, $R^2$ and $R^3$ correspond to R, $R^1$, $R^2$ and $R^3$ in the formula (1), respectively, and are defined as above.

Preferable examples of the dialkylamine to be used in the reaction (B) of the present invention include methyl isopropyl amine, ethyl isopropyl amine, n-propyl isopropyl amine, n-butyl isopropyl amine, methyl-t-butyl amine, ethyl-t-butyl amine, n-propyl-t-butyl amine, n-butyl-t-butyl amine, methyl-s-butyl amine, ethyl-s-butyl amine, n-propyl-s-butyl amine, n-butyl-s-butyl amine, methyl-t-amyl amine, ethyl-t-amyl amine, n-propyl-t-amyl amine and n-butyl-t-amyl amine. Among them, methyl isopropyl amine, ethyl isopropyl amine, n-propyl isopropyl amine, methyl-t-butyl amine, ethyl-t-butyl amine, n-propyl-t-butyl amine, methyl-s-butyl amine, ethyl-s-butyl amine or n-propyl-s-butyl amine may be more preferably used.

The amount of the dialkylamine to be used may be preferably from 2.0 mole to 10.0 mole, more preferably from 2.5 mole to 6.0 mole, per mole of the aluminum hydride compound or the alkyl aluminum compound.

The reaction (B) of the present invention may be preferably conducted in an organic solvent. The organic solvent to be used is not limited as long as it does not inhibit the reaction.

Examples thereof include ethers such as diethyl ether, tetrahydrofuran, dimethoxyethane and dioxane; aliphatic hydrocarbons such as hexane, heptane, cyclohexane, methylcyclohexane and ethylcyclohexane; and aromatic hydrocarbons such as toluene and xylene. An ether, an aliphatic hydrocarbon, or a mixture of an ether and an aliphatic hydrocarbon may be suitably used. These organic solvents may be used alone or in combination of two or more types thereof.

The amount of the organic solvent to be used may be preferably from 1 g to 100 g, more preferably from 1 g to 50 g, per gram (g) of the aluminum hydride compound or the alkyl aluminum compound.

The reaction (B) of the present invention may be conducted, for example, by a method in which dialkylamine and aluminum hydride compound, or alternatively, alkyl aluminum compound, and an organic solvent are mixed, and the resultant mixture is reacted while stirring. The reaction temperature may be preferably from −100° C. to 100° C., more preferably from −80° C. to 40° C. There are no particular restrictions to the reaction pressure.

The tris(dialkylamide)aluminum compound, which is the desired product, may be obtained by the reaction (A) or (B) of the present invention. After the completion of the reaction, the synthesized tris(dialkylamide)aluminum compound may be isolated/purified by a known method such as extraction, filtration, concentration, distillation, sublimation, recrystallization and column chromatography.

The tris(dialkylamide)aluminum compound, which is the desired product of the present invention, and the aluminum compound, which is the starting material, are often unstable to moisture and oxygen in the atmosphere. Accordingly, the reaction operation, the post-treatment of the reaction solution, and the like may be preferably conducted under anhydrous conditions or under inert gas conditions.

<Method of Producing Dialkylamine Compound as the Ligand of the Present Invention>

The asymmetric dialkylamine compound which serves as the ligand in the tris(dialkylamide)aluminum compound of the present invention and is represented by the formula (4):

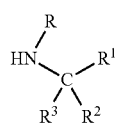

(4)

wherein

R represents a linear alkyl group having 1 to 6 carbon atoms; and $R^1$, $R^2$ and $R^3$ may be the same as, or different from each other, and each independently represents hydrogen atom, or a linear or branched alkyl group having 1 to 6 carbon atoms, or $R^1$, $R^2$ and $R^3$ may be joined together to form a ring, with the proviso that the compounds in which two or more of $R^1$, $R^2$ and $R^3$ are hydrogen atoms are excluded, may be obtained, for example, by a production process comprising the following two steps of:

(A) mixing an aryl methylidene amine compound represented by the formula (4-1):

(4-1)

wherein

Ar represents an aryl group; and $R^1$, $R^2$ and $R^3$ are defined as above, and an organic solvent; and then adding an alkylating agent to the mixture solution, while maintaining the mixture solution at 75° C.-110° C., preferably in an amount of from 0.90 mol to 1.20 mol relative to 1 mol of the aryl methylidene amine compound, and reacting the mixture, thereby producing a reaction solution containing the asymmetric dialkylamine compound represented by the formula (4); and (B) adding water to the reaction solution, and mixing them, and then separating the water layer; and then mixing the water layer obtained and a basic aqueous solution, and then separating the organic layer, and obtaining the asymmetric dialkylamine compound represented by the formula (4) from the organic layer.

[(A) Step of Producing a Reaction Solution Containing the Asymmetric Dialkylamine Compound (Hereinafter, Sometimes Referred to as "Step A1")]

The aryl methylidene amine compound to be used in Step A of the present invention is represented by the formula (4-1). In the formula (4-1), Ar represents an aryl group which may have a substituent. Examples of the Ar include aryl group having 6 to 14 carbon atoms such as phenyl, tolyl, methoxyphenyl, fluorophenyl, chlorophenyl, mesityl, naphthyl and anthryl. Among them, phenyl and tolyl may be preferred.

$R^1$, $R^2$ and $R^3$ correspond to $R^1$, $R^2$ and $R^3$ in the formula (1), respectively, and $R^1$, $R^2$ and $R^3$ represent hydrogen atom, or a linear or branched alkyl group having 1 to 6 carbon atoms, or $R^1$, $R^2$ and $R^3$ may be joined together to form a ring. However, the cases where two or more of $R^1$, $R^2$ and $R^3$ are hydrogen atoms are excluded.

The organic solvent to be used in Step A of the present invention may be preferably at least one selected from the group consisting of aliphatic hydrocarbons (including alicyclic hydrocarbons), halogenated aliphatic hydrocarbons, aromatic hydrocarbons and halogenated aromatic hydrocarbons. More specifically, examples of the organic solvent include aliphatic hydrocarbons such as pentane, hexane, heptane, octane, cyclohexane and cycloheptane; halogenated aliphatic hydrocarbons such as methylene chloride, chloroform, carbon tetrachloride and 1,2-dichloroethane; aromatic hydrocarbons such as benzene, toluene, xylene and mesitylene; and halogenated aromatic hydrocarbons such as chlorobenzene and dichlorobenzene.

The amount of the organic solvent to be used may be preferably from 0.10 mole to 0.80 mole, more preferably from 0.20 mole to 0.50 mole, per mole of the aryl methylidene amine compound. When the amount of the organic solvent falls within the above-mentioned range, solidification of the reaction solution may be prevented, while maintaining the high reaction rate.

Examples of the alkylating agent to be used in Step A of the present invention include dialkyl sulfates such as dimethyl sulfate and diethyl sulfate; halogenated alkyls such as methyl iodide; diazoalkanes such as diazomethane; and alkyl esters such as alkyl carbonate and dialkyl oxalate. Among them, dialkyl sulfate may be preferably used. The alkyl group contained in the alkylating agent such as dialkyl sulfate will be converted into the R group (linear alkyl group having 1 to 6 carbon atoms) in the asymmetric dialkylamine compound represented by the formula (4).

The amount of the alkylating agent to be used may be preferably from 0.90 mole to 1.20 mole, more preferably from 0.95 mole to 1.05 mole, per mole of the aryl methylidene amine compound. When the amount of the alkylating agent falls within the above-mentioned range, the unreacted alkylating agent and the by-product(s) may be easily treated from the reaction solution after the reaction, while maintaining the high reaction rate.

In Step A of the present invention, an aryl methylidene amine compound and an organic solvent are mixed, and then, while maintaining the mixture solution at 75° C.-110° C., an alkylating agent is added to the mixture solution preferably in an amount of from 0.90 mol to 1.20 mol relative to 1 mol of the aryl methylidene amine compound, and the aryl methylidene amine compound is reacted with the alkylating agent at the same temperature (75° C.-110° C.). There are no particular restrictions to the reaction pressure.

The reaction solution obtained in Step A, which contains the asymmetric dialkylamine compound represented by the formula (4), may be used in the subsequent step(s) without any treatment.

In addition, the aryl methylidene amine compound represented by the formula (4-1), which is to be used in Step A of the present invention, may be obtained by reacting a monoalkylamine represented by the formula (4-2):

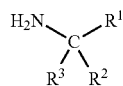

(4-2)

wherein $R^1$, $R^2$ and $R^3$ are defined as above,
with an aryl aldehyde represented by the formula (4.3):

ArCHO (4-3)

wherein Ar is defined as above.
(See Reference Example L-1 described later.)
[(B) Step of Obtaining the Asymmetric Dialkylamine Compound (Hereinafter, Sometimes Referred to as "Step B")]

Step B of the present invention is a step in which the asymmetric dialkylamine compound present in the reaction solution obtained in Step A is obtained (isolated) from the reaction solution without degrading the compound by the side reaction(s) or the successive reaction(s) and without involving the by-product(s). Step B is performed in accordance with the flow diagram as shown by the following.

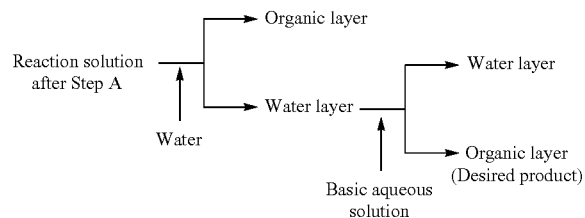

In Step B of the present invention, firstly water is added to, and mixed with the reaction solution, and then the water layer is separated. The amount of water to be used may be preferably from 1 mole to 20 mole, more preferably from 2 mole to 10 mole, per mole of the aryl methylidene amine compound. When the amount of water falls within the above-mentioned range, the by-product derived from the alkylating agent in the reaction solution obtained in Step A (for example, in the case where the alkylating agent is dimethyl sulfate, the salt of methyl sulfate) may readily decompose, and the water layer may be more easily separated from the organic layer. The water layer may contain a salt which is not concerned with the desired product.

The separation of the water layer, which contains the asymmetric dialkylamine compound as the desired product, and the organic layer may be conducted by a commonly-used method, for example, using a separating funnel, and the like. The water layer obtained may be washed with a hydrophobic solvent, as necessary. Examples of the hydrophobic solvent to be used include aliphatic hydrocarbons such as pentane, hexane, heptane, octane, cyclohexane and cycloheptane; halogenated aliphatic hydrocarbons such as methylene chloride, chloroform, carbon tetrachloride and 1,2-dichloroethane; aromatic hydrocarbons such as benzene, toluene, xylene and mesitylene; and halogenated aromatic hydrocarbons such as chlorobenzene and dichlorobenzene.

And then, the water layer obtained by the separation is mixed with a basic aqueous solution. The amount of base in the basic aqueous solution to be used may be preferably from 1.00 mole to 5.00 mole, more preferably from 1.85 mole to 2.20 mole, per mole of the aryl methylidene amine compound. When the amount of base falls within the above-mentioned range, the by-product derived from the alkylating agent (for example, in the case where the alkylating agent is dimethyl sulfate, the salt of methyl sulfate) may readily decompose, and the movement of the asymmetric dialkylamine compound as the desired product into the water layer, i.e. the loss of the desired product may be prevented. Additionally, the organic layer may be more easily separated from the water layer containing a residue of the alkylating agent which may cause the side reaction(s) or the successive reaction(s), and thereby the loss of the asymmetric dialkylamine compound caused by the reaction(s) may be prevented.

In addition, the concentration of the basic aqueous solution may be preferably from 15 wt % to 48 wt %, more preferably from 25 wt % to 40 wt %. When the concentration falls within the above-mentioned range, the by-product derived from the alkylating agent (for example, in the case where the alkylating agent is dimethyl sulfate, the salt of methyl sulfate) may be removed into the water layer, and the loss of the asymmetric dialkylamine compound as the desired product into the water layer may be prevented. Additionally, the organic layer may be more easily separated from the water layer containing a residue of the alkylating agent which may cause the side reaction(s) or the successive reaction(s), and thereby the loss of the asymmetric dialkylamine compound caused by the reaction(s) may be prevented.

An aqueous solution of an alkali metal hydroxide such as sodium hydroxide, for example, may be used as the basic aqueous solution to be used in Step B of the present invention.

And then, the organic layer, which contains the asymmetric dialkylamine compound as the desired product, is separated. The separation may be conducted by a commonly-used method, for example, using a separating funnel, and the like.

Although the organic layer contains the asymmetric dialkylamine compound, which is the desired product, as the principal component, purification may be preferably conducted to remove the by-product(s) and enhance the purity of the desired product.

The method of purification may be appropriately selected depending on the melting point and the boiling point of the desired product, and the like. The product may be distilled under atmospheric pressure, reduced pressure, or increased pressure, for example, to reduce the amount of the by-product(s) such as tertiary amine and water. Although the distillation conditions are not limited, the distillation may be preferably conducted under milder conditions, for example, at a distillation temperature of 25° C.-90° C. in a shorter time when the product contains a compound which may cause the side reaction(s) or the successive reaction(s) (the alkylating agent, and the residue thereof, for example).

The asymmetric dialkylamine compound represented by the formula (4) may be obtained by Step B as described above. The asymmetric dialkylamine compound may be obtained in high yield without performing a complicated operation by the method. For example, there may be provided a material composition which contains the trialkylamine as the by-product in an amount of less than 5%, the monoalkylamine as the decomposition product of the raw material in an amount of less than 3%, and the alkyl alcohol as the by-product from the alkylating agent in an amount of less than 3%, and which is suitable for the raw material for production of the tris(dialkylamide)aluminum compound of the present invention.

<Method of Producing Aluminum-Containing Thin Film of the Present Invention>

An aluminum-containing thin film may be formed with good film-forming performance by a CVD method, for example, using the tris(dialkylamide)aluminum compound of the present invention.

An aluminum-containing thin film may be vapor-deposited on an object by a known CVD method and atomic layer deposition method (ALD method). For example, an aluminum-containing thin film may be vapor-deposited on an object by feeding the vapor of the tris(dialkylamide)aluminum compound onto the heated object under atmospheric or reduced pressure, together with a reactive gas (for example, an oxidizing gas such as oxygen and ozone; water; alcohols such as methanol, ethanol, n-propyl alcohol, isopropyl alcohol and n-butanol; nitrogen-containing gas such as ammonia and hydrazine; hydrogen). The gas (including a vaporized liquid) may be diluted with an inert gas, and the like. An aluminum-containing thin film may be also vapor-deposited by a plasma CVD method in which the similar material is fed.

In the CVD method, the tris(dialkylamide)aluminum compound needs to be vaporized for the formation of thin film. A method of vaporizing the tris(dialkylamide)aluminum compound to be employed in the present invention may be, for example, a method in which the tris(dialkylamide)aluminum compound itself is filled or fed into a vaporizing chamber, and then vaporized therein, or alternatively, a method (solution method) in which a solution prepared by diluting the tris(dialkylamide)aluminum compound with a suitable solvent (Examples thereof include aliphatic hydrocarbons such as hexane, cyclohexane, methylcyclohexane, ethylcyclohexane, heptane and octane; aromatic hydrocarbons such as toluene, ethyl benzene and xylene; and ethers such as glyme, diglyme, triglyme, dioxane and tetrahydrofuran) is fed into a vaporizing chamber with a liquid feed pump, and then vaporized therein.

As for the vapor-deposition conditions in the case where an aluminum-containing thin film is vapor-deposited using the tris(dialkylamide)aluminum compound of the present invention, for example, the pressure in the reaction system may be preferably from 1 Pa to 200 kPa, more preferably from 10 Pa to 110 kPa, the temperature of the object on which the film is formed may be preferably from 50° C. to 900° C., more preferably from 100° C. to 600° C., and the temperature at which the tris(dialkylamide)aluminum compound is vaporized may be preferably from 30° C. to 250° C., more preferably from 60° C. to 200° C.

When an aluminum-containing thin film is vapor-deposited, the percentage of an oxygen source (an oxidizing gas, water vapor or alcohol vapor, or a mixture thereof, for example) or a reducing gas (hydrogen gas or ammonia gas, or a mixture thereof, for example) to the total amount of the gases may be preferably from 3 vol % to 99 vol %, more preferably from 5 vol % to 98 vol %.

EXAMPLES

The present invention will be more specifically described below with reference to the Examples. However, the scope of the present invention should not be limited to these Examples.

Example 1

Method (A); Synthesis of tris(methyl isopropyl amide)aluminum (Compound (6))

30.1 g (70.5 mmol) of 15% butyl lithium/hexane solution was placed into a 100 mL-volume flask equipped with a stirrer, a thermometer and a dropping funnel, and then was cooled down. Subsequently, 6.8 g (93.4 mmol) of methyl isopropyl amine was slowly dropped into the flask such that the internal temperature was maintained at 0° C.-6° C., and the resultant mixture was stirred for 30 min, and then the solution was concentrated. Subsequently, 35 ml of diethyl ether was added to the resultant concentrate, and then 3.0 g (22.4 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (170° C., 51 Pa), to provide 4.1 g of tris(methyl isopropyl amide)aluminum as a viscous pale-yellow liquid. (Isolation yield; 70.5%)

Additionally, tris(methyl isopropyl amide)aluminum was a novel compound, which had the following properties:

$^1$H-NMR ($C_6H_6$, δ (ppm)); 1.06-1.12 (12H, m), 1.22-1.27 (24H, m), 2.33-2.78 (18H, m), 3.27-3.90 (6H, s)

The vapor pressure estimated from the distillation temperature and the distillation rate was 1 Torr at about 160° C.

Example 2

Method (A); Synthesis of tris(ethyl isopropyl amide)aluminum (Compound (7))

30.6 g (71.6 mmol) of 15% butyl lithium/hexane solution was placed into a 100 mL-volume flask equipped with a stirrer, a thermometer and a dropping funnel, and then was cooled down. Subsequently, 7.8 g (89.5 mmol) of ethyl isopropyl amine was slowly dropped into the flask such that the internal temperature was maintained at −3° C.-2° C., and the resultant mixture was stirred for 30 min, and then the solution was concentrated. Subsequently, 35 ml of diethyl ether was added to the resultant concentrate, and then 3.0 g (22.1 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (110° C., 45 Pa), to provide 1.7 g of tris(ethyl isopropyl amide)aluminum as a pale-yellow liquid. (Isolation yield; 26.6%)

Additionally, tris(ethyl isopropyl amide)aluminum was a novel compound, which had the following properties:

$^1$H-NMR (C$_6$H$_6$, δ (ppm)); 1.16-1.21 (27H, m), 2.91 (6H, q), 3.30-3.39 (3H, m)
Viscosity; 7.93 cP (24° C.)
Spontaneous combustibility (in the air at a temperature of 25° C. and a humidity of 60%); Spontaneous combustion did not occur.
Vapor pressure (70° C.); 1.1 Torr Example 3

Method (A); Synthesis of tris(methyl-t-butyl amide)aluminum (Compound (14))

35.7 g (83.6 mmol) of 15% butyl lithium/hexane solution and toluene (30 ml) were placed into a 100 mL-volume flask equipped with a stirrer, a thermometer and a dropping funnel, and then were cooled down. Subsequently, 7.4 g (84.3 mmol) of methyl-t-butyl amine was slowly dropped into the flask such that the internal temperature was maintained at −20° C.--15° C., and the resultant mixture was stirred at room temperature for 1 hr, and then the solution was concentrated. Subsequently, 30 ml of diethyl ether was added to the resultant concentrate, and then 3.6 g (27.0 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (100° C., 40 Pa), to provide 6.7 g of tris(methyl-t-butyl amide)aluminum as a white solid. (Isolation yield; 87.4%)

Additionally, tris(methyl-t-butyl amide)aluminum was a novel compound, which had the following properties:

$^1$H-NMR (C$_6$H$_6$, δ (ppm)); 1.22 (27H, s), 2.58 (9H, s)
Melting point; 45-50° C.
Spontaneous combustibility (in the air at a temperature of 22° C. and a humidity of 50%); Spontaneous combustion did not occur.
Vapor pressure (80° C.); 1.1 Torr Example 3-1

Method (A); Synthesis of tris(methyl-t-butyl amide)aluminum (Compound (14))

1694.4 g (4.14 mol) of 15.65% butyl lithium/hexane solution was placed into a 3 L-volume flask equipped with a stirrer, a thermometer and a dropping funnel, and then was cooled down. Subsequently, 382.6 g (4.39 mol) of methyl-t-butyl amine was slowly dropped into the flask such that the internal temperature was maintained at 3° C.-5° C. Then, 250 ml of cyclopentyl methyl ether was added to the mixture, and the resultant mixture was stirred at room temperature for 30 min, and then the solution was concentrated. Subsequently, 550 ml of cyclopentyl methyl ether was added to the resultant concentrate, and then 180.2 g (1.35 mol) of anhydrous aluminum chloride dissolved in 800 ml of cyclopentyl methyl ether was slowly dropped into the mixture under water-cooling, and the resultant mixture was reacted at room temperature for 30 min. After the completion of the reaction, the reaction solution was concentrated, and then the resultant concentrate was distilled under reduced pressure (120° C., 35 Pa), to provide 369.3 g of tris(methyl-t-butyl amide)aluminum as a white solid. (Isolation yield; 95.7%)

Example 3-2

Method (A); Synthesis of tris(methyl-t-butyl amide)aluminum (Compound (14))

406.2 g (0.99 mol) of 15.65% butyl lithium/hexane solution was placed into a 1 L-volume flask equipped with a stirrer, a thermometer and a dropping funnel, and then was cooled down. Subsequently, 91.1 g (1.05 mol) of methyl-t-butyl amine was slowly dropped into the flask such that the internal temperature was maintained at 4° C.-7° C. Then, 50 ml of cyclopentyl methyl ether was added to the mixture, and the resultant mixture was stirred at room temperature for 30 min, and then the solution was concentrated. Subsequently, 140 ml of cyclopentyl methyl ether was added to the resultant concentrate, and then 43.1 g (0.32 mol) of anhydrous aluminum chloride dissolved in 190 ml of cyclopentyl methyl ether was slowly dropped into the mixture under water-cooling, and the resultant mixture was reacted at room temperature for 30 min. After the completion of the reaction, the reaction solution was concentrated, and then 350 ml of hexane was added to the resultant concentrate, and the mixture solution was filtrated under pressure. The precipitate was washed with hexane, and then all the filtrate was concentrated. The resultant concentrate was distilled under reduced pressure (110° C., 14 Pa), to provide 85.1 g of tris(methyl-t-butyl amide)aluminum as a white solid. (Isolation yield; 92.3%)

Example 4

Method (A); Synthesis of tris(ethyl-t-butyl amide)aluminum (Compound (15))

30.1 g (70.5 mmol) of 15% butyl lithium/hexane solution was placed into a 100 mL-volume flask equipped with a stirrer, a thermometer and a dropping funnel, and then was cooled down. Subsequently, 8.4 g (82.9 mmol) of ethyl-t-butyl amine was slowly dropped into the flask such that the internal temperature was maintained at −10° C.--5° C., and the resultant mixture was stirred at 20° C. for 30 min, and then the solution was concentrated. Subsequently, 30 ml of diethyl ether was added to the resultant concentrate, and then 2.9 g (21.5 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (140° C., 40 Pa), to provide 3.5 g of tris(ethyl-t-butyl amide)aluminum as a pale-yellow liquid. (Isolation yield; 50.1%)

Additionally, tris(ethyl-t-butyl amide)aluminum was a novel compound, which had the following properties:

$^1$H-NMR (C$_6$H$_6$, δ (ppm)); 1.26 (36H, m), 2.98 (6H, q)
The vapor pressure estimated from the distillation temperature and the distillation rate was 1 Torr at about 130° C.

Comparative Example 1

Method (A); Synthesis of tris(dimethyl amide)aluminum (tris(dialkylamide)aluminum Compound Represented by the Formula (1) in which R=—CH$_3$, R$^1$=H, R$^2$=H, R$^3$=H)

107.9 g (252.6 mmol) of 15% butyl lithium/hexane solution was placed into a 300 mL-volume flask equipped with a stirrer, a thermometer and a dropping funnel, and then was cooled down. Subsequently, 19.3 g (427.0 mmol) of dimethyl amine was slowly dropped into the flask such that the internal temperature was maintained at 0° C.-6° C., and the resultant mixture was stirred for 30 min, and then the solution was concentrated. Subsequently, 150 ml of diethyl ether was added to the resultant concentrate, and then 10.7 g (80.5 mmol) of anhydrous aluminum chloride dissolved in 60 ml of diethyl ether was slowly dropped into the mixture under water cooling, and the resultant mixture was reacted at room temperature for 2 hr. After the completion of the reaction, the reaction solution was concentrated, and then the resultant concentrate was distilled under reduced pressure (110° C., 37 Pa), to provide 10.3 g of tris(dimethyl amide)aluminum as a white solid. (Isolation yield; 80.2%)

$^1$H-NMR ($C_6H_6$, δ (ppm)); 2.33 (6H, s), 2.69 (12H, s)
Melting point; 82-84° C.
Vapor pressure (70° C.); 0.1 Torr
Vapor pressure (105° C.); 1.1 Torr This compound had lower vapor pressure than the compound of Example 2.

Comparative Example 2

Method (A); Synthesis of tris(methyl isobutyl amide) aluminum (tris(dialkylamide)aluminum Compound Represented by the Formula (1) in which R=—$CH_3$, $R^1$=—CH($CH_3$)$_2$, $R^2$=H, $R^3$=H)

37.1 g (86.8 mmol) of 15% butyl lithium/hexane solution and toluene (30 ml) were placed into a 100 mL-volume flask equipped with a stirrer, a thermometer and a dropping funnel, and then were cooled down. Subsequently, 8.5 g (97.5 mmol) of methyl isobutyl amine was slowly dropped into the flask such that the internal temperature was maintained at −20° C.-−10° C., and the resultant mixture was stirred at room temperature for 30 min, and then the solution was concentrated. Subsequently, 30 ml of diethyl ether was added to the resultant concentrate, and then 3.7 g (27.7 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (180° C., 37 Pa), to provide 5.3 g of tris(methyl isobutyl amide)aluminum as a highly-viscous yellow liquid. (Isolation yield; 67.6%)

Additionally, tris(methyl isobutyl amide)aluminum had the following properties:
$^1$H-NMR ($C_6H_6$, δ (ppm)); 0.9-1.1 (18H, m), 1.8-2.3 (3H, m), 2.4-3.2 (15H, m)

The vapor pressure estimated from the distillation temperature and the distillation rate was 1 Torr at about 180° C., and this compound had lower vapor pressure than the compounds of Examples 1 and 4.

Comparative Example 3

Method (A); Synthesis of tris(diethyl amide)aluminum (tris(dialkylamide)aluminum Compound Represented by the Formula (1) in which R=—$C_2H_5$, $R^1$=—$CH_3$, $R^2$=H, $R^3$=H)

31.8 g (74.4 mmol) of 15% butyl lithium/hexane solution was placed into a 100 mL-volume flask equipped with a stirrer, a thermometer and a dropping funnel, and then was cooled down. Subsequently, 6.8 g (93.0 mmol) of diethyl amine was slowly dropped into the flask such that the internal temperature was maintained at −2° C.-2° C., and the resultant mixture was stirred for 30 min, and then the solution was concentrated. Subsequently, 35 ml of diethyl ether was added to the resultant concentrate, and then 3.1 g (23.0 mmol) of anhydrous aluminum chloride dissolved in 30 ml of diethyl ether was slowly dropped into the mixture under water-cooling, and the resultant mixture was reacted at room temperature for 1 hr. After the completion of the reaction, the reaction solution was concentrated, and then the resultant concentrate was distilled under reduced pressure (150° C., 45 Pa), to provide 4.7 g of tris(diethyl amide)aluminum as a viscous yellow liquid. (Isolation yield; 84.4%)

$^1$H-NMR ($C_6H_6$, δ (ppm)); 1.02-1.28 (18H, m), 2.88-3.32 (12H, m)

The vapor pressure estimated from the distillation temperature and the distillation rate was 1 Torr at about 150° C.

The distillation conditions and the vapor pressures of the aluminum compounds obtained in Examples 1-4 and Comparative Examples 1-3 are shown in Table A.

TABLE A

| | Compound | | Distillation conditions | Vapor pressure |
|---|---|---|---|---|
| Example 1 | tris(methyl isopropyl amide)aluminum | Compound (6) | 170° C., 51 Pa | about 160° C.; 1 Torr |
| Example 2 | tris(ethyl isopropyl amide)aluminum | Compound (7) | 110° C., 45 Pa | 70° C.; 1.1 Torr |
| Example 3 | tris(methyl-t-butyl amide)aluminum | Compound (14) | 100° C., 40 Pa | 80° C.; 1.1 Torr |
| Example 4 | tris(ethyl-t-butyl amide)aluminum | Compound (15) | 140° C., 40 Pa | about 130° C.; 1 Torr |
| Comparative Example 1 | tris(dimethyl amide)aluminum | | 110° C., 37 Pa | 105° C.; 1.1 Torr |
| Comparative Example 2 | tris(methyl isobutyl amide)aluminum | | 180° C., 37 Pa | about 180° C.; 1 Torr |
| Comparative Example 3 | tris(diethyl amide)aluminum | | 150° C., 45 Pa | about 150° C.; 1 Torr |

It is assumed from the results that the tris(dialkylamide) aluminum compounds of the present invention are compounds from which an aluminum-containing thin film may be easily produced on an object by a CVD method, because of high vapor pressure, without the risk of clogging of pipe, because of low melting point.

Example 5

Vapor-Deposition Test; Formation of Aluminum-Containing Thin Film

The vapor-deposition test was conducted by the CVD method, using the aluminum compound (14) obtained in Example 3, to evaluate the film-forming performance.

The apparatus shown in FIG. 1 was used to conduct the evaluation tests. The aluminum compound 20 in a vaporizer (glass ampule) 3 is heated by means of a heater 10B and vaporized, and is discharged from the vaporizer 3, together with a helium gas which is fed via a mass flow controller 1A after pre-heated by a pre-heater 10A. The gas discharged from the vaporizer 3 is fed into a reactor 4, together with an ammonia gas or a hydrogen gas or an oxygen gas, which is fed via a mass flow controller 1B and a stop valve 2. The pressure in the reaction system is controlled to a predetermined pressure by opening and closing a valve 6, which is provided upstream of a vacuum pump, and is monitored by a pressure gauge 5. The central part of the reactor can be heated by a heater 10C. The aluminum compound, which is fed into the reactor, is reductively or oxidatively thermally-decomposed on a surface of a substrate 21 which is placed in the central part of the reactor and heated to a predetermined temperature by the heater 10C, to deposit an aluminum-containing thin film on the substrate 21. The gas discharged from the reactor 4 is exhausted to the atmosphere via a trap 7 and the vacuum pump.

The vapor-deposition conditions and the vapor-deposition results (film properties) were as follows. The rectangular substrate of 6 mm×20 mm was used as the substrate on which the film was vapor-deposited.

(Vapor-Deposition Conditions)
Aluminum raw material; tris(methyl-t-butyl amide)aluminum (Compound (14))
Raw material feed conditions; feeding aluminum raw material and ammonia by turns
Vaporization temperature; 60° C.
Aluminum raw material He carrier gas flow rate; 10 sccm
Aluminum raw material feed time; 1 min
Aluminum raw material feed pressure; 0.67 kPa
Ammonia gas flow rate; 10 sccm
Ammonia feed time; 1 min
Ammonia feed pressure; 0.67 kPa
Purge time; 30 sec
Purge pressure; 0.17 kPa
Number of cycles; 20 times
Substrate material; $SiO_2$/Si wafer
Substrate temperature; 450° C.
(Film Properties (SEM and XPS-Depth Measurement))
Film thickness; 600 nm (1 cycle; 30 nm)
XPS analysis; Aluminum nitride film
Carbon content; Not detected The results revealed that a high-quality aluminum nitride film, which did not contain impurities such as carbon atom, might be formed from the tris(dialkylamide)aluminum compound of the present invention.

Example 6

Vapor-Deposition Test; Formation of Aluminum-Containing Thin Film

The vapor-deposition test was conducted by the CVD method, using tris(methyl-t-butyl amide)aluminum (Compound (14)) obtained in Example 3, to evaluate the film-forming performance. The vapor-deposition conditions and the film properties were as follows.

(Vapor-Deposition Conditions)
Aluminum raw material; tris(methyl-t-butyl amide)aluminum (Compound (14))
Vaporization temperature; 60° C.
He carrier gas flow rate; 10 sccm
Oxygen gas flow rate; 5 sccm
Film-formation time; 10 min
Substrate material; $SiO_2$/Si wafer
Substrate temperature; 200° C.

Pressure in the reaction system; 0.67 kPa
(Film Properties (SEM and XPS-Depth Measurement))
Film thickness; 200 nm
XPS analysis; Aluminum oxide film
Carbon content; Not detected
Nitrogen content; Not detected The results revealed that a high-quality aluminum oxide film, which did not contain impurities such as carbon atom, might be formed from the tris(dialkylamide)aluminum compound of the present invention.

Reference Example L-1

Synthesis of N-benzylidene-t-butyl amine

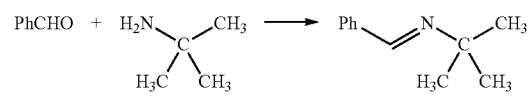

530.85 g (5.00 mol) of benzaldehyde was placed into a 2000 mL-volume flask equipped with a stirrer, a thermometer and a dropping funnel. Subsequently, 367.50 g (5.02 mol) of t-butyl amine was dropped into the flask in a water bath, while maintaining the solution temperature at 25° C. After the completion of the dropping, the mixture was reacted while stirring at 25° C. for 15 hours. After the completion of the reaction, the reaction mixture was subjected to separation, and the organic layer obtained was refluxed under reduced pressure (25° C., 13.3 Pa) for 2 hours, to provide 788.91 g of N-benzylidene-t-butyl amine. (Isolation yield; 98%)

Example L-1

Synthesis of t-butyl(methyl)amine

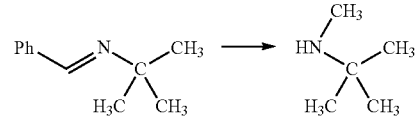

(Step A)

Under argon atmosphere, 89.18 g (0.553 mol) of N-benzylidene-t-butyl amine, which was prepared in the same way as in Reference Example L-1, and 16.82 g (0.183 mol) of toluene were placed into a 200 mL-volume flask equipped with a stirrer, a thermometer and a dropping funnel. Subsequently, 69.76 g (0.553 mol) of dimethyl sulfate was slowly dropped into the flask, while maintaining the mixture solution at 85° C.-90° C. After the completion of the dropping, the mixture solution was reacted while stirring at 85° C.-90° C. for 2 hours.

(Step B)

After the completion of the reaction, 48.34 g (2.683 mol) of water was slowly dropped into the reaction solution, while maintaining the solution at 85° C.-90° C., and then the reaction solution was subjected to separation at room temperature, and the water layer was obtained. The water layer obtained was washed with toluene. And then, 124.25 g (1.106 mol) of 36 wt % sodium hydroxide aqueous solution was placed into a 300 mL-volume flask equipped with a stirrer, a thermometer and a dropping funnel, and the water layer obtained earlier was slowly dropped into the flask, while maintaining the solution temperature at 10° C.-15° C., and then the reaction solution was subjected to separation. The organic layer obtained was distilled under atmospheric pressure (68° C.-71° C.), to provide 44.83 g of t-butyl(methyl) amine. (Isolation yield; 84%)

As for the composition of t-butyl(methyl)amine obtained, the content ratio of t-butyl(methyl)amine as the desired product, t-butyl(dimethyl)amine (by-product), t-butyl amine (decomposition product of raw material), and methanol (by-product) was 90.3:1.4:2.7:0.3, and the by-products and the residual raw material were present in very small amounts.

Examples L-2 to L-3, and Comparative Examples L-1 to L-2

The reaction was conducted in the same way as in Example L-1, except that various reaction conditions were changed. The reaction conditions (Steps A and B) are shown in Table 1, and the results of the reactions are shown in Table 2. The various molar ratios (* in the Table) represent molar ratios relative to 1 mol of the aryl methylidene amine compound.

TABLE 1

| | Step A | | | | Step B |
|---|---|---|---|---|---|
| | Amount of organic solvent*) (molar ratio) | Temperature of addition of alkylating agent (° C.) | Amount of alkylating agent*) (molar ratio) | Reaction temperature (° C.) | Amount of base*) (molar ratio) |
| Example L-1 | 0.34 | 84-107 | 1.00 | 85-90 | 2.0 |
| Example L-2 | 0.43 | 87-94 | 1.00 | 89 | 2.2 |
| Example L-3 | 0.34 | 79-85 | 1.20 | 79-83 | 2.1 |
| Comparative Example L-1 | 0 | 58-62 | 1.20 | 58-60 | 2.3 |
| Comparative Example L-2 | 1.49 | 58-60 | 1.20 | 60-80 | 2.3 |

TABLE 2

| | Reaction yield (%) | | Composition ratio of product (%) | | | |
|---|---|---|---|---|---|---|
| | Imine conversion (%) | t-butyl (methyl) amine (desired product) | t-butyl (methyl) amine (desired product) | t-butyl (dimethyl) amine (by-product) | t-butyl amine (raw material) | methanol (by-product) |
| Example L-1 | 97 | 84 | 90.3 | 1.4 | 2.7 | 0.3 |
| Example L-2 | 97 | 83 | 89.4 | 1.4 | 2.4 | 0.1 |
| Example L-3 | 98 | 77 | 91.6 | 3.0 | 1.0 | 1.0 |
| Comparative Example L-1 | 70 | 63 | 87.8 | 6.2 | 3.0 | 0.2 |
| Comparative Example L-2 | 64 | 37 | 70.5 | 0.6 | 0.6 | 0.1 |

INDUSTRIAL APPLICABILITY

An aluminum-containing thin film may be produced on an object with good film-forming performance by a CVD method using the novel tris(dialkylamide)aluminum compound of the present invention. The tris(dialkylamide)aluminum compound of the present invention is a useful compound as a material for the formation of aluminum-containing thin film, and, for example, as a material for the production of polymerization catalysts, medicines, agricultural chemicals, and the like.

DESCRIPTION OF REFERENCE NUMERALS

3. Vaporizer
4. Reactor
10B. Heater for vaporizer
10C. Heater for reactor
20. Aluminum compound melt
21. Substrate

The invention claimed is:

1. A tris(dialkylamide)aluminum compound represented by the formula (1):

(1)

wherein
R represents ethyl, $R^1$ and $R^2$ represent methyl, and $R^3$ represents hydrogen atom; or
R represents methyl, and $R^1$, $R^2$ and $R^3$ represent methyl.

* * * * *